United States Patent
Xie et al.

(10) Patent No.: US 8,466,131 B2
(45) Date of Patent: Jun. 18, 2013

(54) LIGANDS SPECIFIC FOR CANNABINOID RECEPTOR SUBTYPE 2

(75) Inventors: Xiangqun Xie, Pittsburgh, PA (US); Jianzhong Chen, Pittsburgh, PA (US); Yuxun Zhang, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 203 days.

(21) Appl. No.: 12/740,099

(22) PCT Filed: Oct. 31, 2008

(86) PCT No.: PCT/US2008/012395
§ 371 (c)(1), (2), (4) Date: Jan. 20, 2011

(87) PCT Pub. No.: WO2009/058377
PCT Pub. Date: May 7, 2009

(65) Prior Publication Data
US 2011/0118214 A1    May 19, 2011

Related U.S. Application Data

(60) Provisional application No. 60/984,461, filed on Nov. 1, 2007.

(51) Int. Cl.
*A61K 31/655* (2006.01)
*C09B 29/33* (2006.01)

(52) U.S. Cl.
USPC ............. 514/150; 534/739; 534/886

(58) Field of Classification Search
None
See application file for complete search history.

(56) References Cited

U.S. PATENT DOCUMENTS
2005/0054679 A1    3/2005    Kruse et al.
2006/0172019 A1    8/2006    Ralston et al.

FOREIGN PATENT DOCUMENTS
WO    WO 03/059064    * 7/2003

OTHER PUBLICATIONS

Registry No. 5466-73-9, entered into Registry file on STN on Nov. 16, 1984.*
PubChem BioAssay Data MLS002639109 [CID 230943], http://pubchem.ncbi.nlm.nih.gov/assay/assay.cgi?cid=230943&ocfilter=act, downloaded on Jan. 29, 2012.*
Shaw, Elliott et al., "A New and Convenient Synthesis of 4-Amino-5-Imidazolecarboxamide", Journal of Biological Chemistry, 181, 89-93, 1949.*
Belskaya, N.P. et al., "Reactions of 2-Arylhydrazonoacetamidoximes With Orthoesters", Russian Chemical Bulletin, International Edition, 60(5),889-895, May 2011.*
Berseneva, Vera S. et al, "Reactions of Malonthioamides and Malonamidines With Methyl Acetylpyruvate as a One-Step Method to Prepare 4-Thio- and 4-Aminopyrrolo[3,4-c]pyridines", Tetrahedron, 63, 4491-4496, 2007.*
Xie, Xiang-Qun et al, "3D Structural Model of the G-Protein-Coupled Cannabinoid CB2 Receptor", Proteins: Structure, Function, and Genetics, 53:307-319, 2003.*
International Search Report PCT/US08/12395 dated Jan. 30, 2009.

* cited by examiner

*Primary Examiner* — Michael Barker
(74) *Attorney, Agent, or Firm* — Foley & Lardner LLP

(57) ABSTRACT

A compound of Formula I: (I) has activity as a cannabinoid receptor antagonist. In Formula 1, R1 is unsubstituted or substituted aryl, unsubstituted or substituted cycloalkyl, unsubstituted or substituted heterocyclyl, unsubstituted or substituted aralkyl, or unsubstituted or substituted heteroaryl; R2 is unsubstituted or substituted alkyl, unsubstituted or substituted aryl, or unsubstituted or substituted heteroaryl; and R3 is unsubstituted or substituted alkyl, unsubstituted or substituted aralkyl, or unsubstituted or substituted heteroaralkyl; with the proviso that at least one of Ri and R3 is other than unsubstituted aralkyl or R2 is other than unsubstituted aryl.

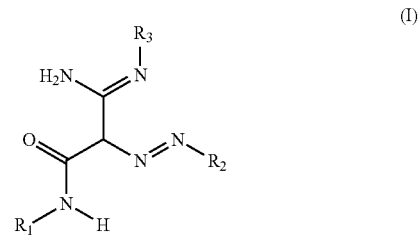

17 Claims, 3 Drawing Sheets

LIGANDS SPECIFIC FOR CANNABINOID RECEPTOR SUBTYPE 2

CROSS-REFERENCE TO RELATED PATENT APPLICATIONS

This application claims priority from U.S. Provisional Application No. 60/984,461, filed Nov. 1, 2007, incorporated herein by reference in its entirety.

GOVERNMENT RIGHTS

The United States Government has rights in this invention pursuant to Contract No. NIH R01 DA015147 between the National Institutes of Health and the University of Pittsburgh.

FIELD OF THE INVENTION

The present invention relates to compounds that bind with specificity to cannabinoid receptor subtype-2 (CB2).

BACKGROUND OF THE INVENTION

Cannabinoid receptor subtypes CB1 (brain) and CB2 (spleen) constitute a category of the important GPCRs drug targets. CB receptors have been implicated in pain transduction and perception as well as neuroinflammation and autoimmune disorders. Finn et al., *Current Neuropharmacology* 2004, 2(1):75-89; and Walter et al., *British Journal of Pharmacology* 2004, 141(5): 775-85. In fact, natural marijuana-derived cannabinoids have been used to relieve pain for millennia. Research publications have demonstrated the analgesic, anti-hyperalgesic and anti-inflammatory actions of selective CB 1 receptor agonists. Howlett et al., *Neuropharmacology* 2004, 47(Suppl. 1): 345-58. Activation of CB1 receptors results, however, in sedation and undesirable psychotropic effects. Efforts have been made to design CB2 ligands that selectively agonize CB2 receptors to treat chronic pain and neuronal disorder diseases without the undesirable effects associated with activation of CB1 receptors in the brain. Malan et al., *Current Opinion in Pharmacology* 2003, 3(1): 62-67.

The CB2 receptor was initially cloned from macrophages and was found to exist predominantly in peripheral areas of the body enriched with B-lymphocytes (e.g., in spleen and lymph nodes). Munro et al., *Nature (London)* 1993, 365(64411): 61-65. The level of CB2 expression in various types of inflammatory cells and immune competent cells is 10-100 times higher than CB1 receptor in these cell types. Galiegue et al., *Eur J Biochem* 1995, 232(1): 54-61; and Carlisle et al., *International Immunopharmacology* 2002, 2(1): 69-82. Cannabinoids exhibit immunosuppressive properties by interfering with humoral immunity, cell-mediated immunity, and cellular defenses against infectious agents. Berdyshev *Chemistry and Physics of Lipids* 2000, 108(1-2): 169-90. Overall, the emerging literature reveals the important roles of the CB2 system and CB2 ligands on immune modulation.

Therapeutic potential of CB ligands has been shown in multiple reviews. Whiteside et al., *Current Medicinal Chemistry* 2007, 14(8): 917-36; Huffman J. W., *Mini-Reviews in Medicinal Chemistry* 2005, 5(7): 641-49; Pertwee R. G., *Pharmacology & Therapeutics* 2002, 95(2): 165-74; Hall et al., *Lancet Oncology* 2005, 6(1): 35-42; Howlett et al., *Neuropharmacology* 2004, 47(Suppl. 1): 345-58; and Carter et al., *Physical Medicine and Rehabilitation Clinics of North America* 2004, 15(4): 943-54, ix. Although CB2 selective compounds have been limited in the clinic, the cannabinoids could potentially be useful in treating autoimmune and immunological disorders (e.g. multiple sclerosis). They have also been studied as anti-inflammatory agents that alleviate inflammatory pain, Mbvundula et al., *Inflammopharmacology* 2004, 12(2): 99-114; Malan et al., *Current Opinion in Pharmacology* 2003, 3(1): 62-67; and Cravatt et al., *Journal of Neurobiology* 2004, 61(1): 149-60, as anti-cancer agents that inhibit the growth of tumors of immune origin as well as glioma tumors and non-melanoma skin cancers, McKallip et al., *Blood* 2002, 100(2): 627-34, and as agents to induce apoptosis in immune system cancer. Bifulco et al., *Recenti Progressi In Medicina* 2003, 94(5):194-98.

It is apparent that the CB2 receptor has a complex involvement involved with the immune system, with tumor cells, and with inflammation. The discovery of CB2 receptors in the CNS contrasts with previous efforts to detect non-CB1 receptors in brain tissue. Van Sickle et al., *Science* 2005, 310 (5746): 329-32. The purpose of these receptors beyond immune cell regulation remains controversial. Still, these studies did open the possibility of non-psychotropic therapeutic interventions, using enhanced endocannabinoid levels localized in the brain, and they offer therapeutic promise for treating central nervous system disorders. Whiteside et al., *Current Medicinal Chemistry* 2007, 14(8): 917-36.

In summary, available evidence suggests that cannabinoids could be valuable, particularly as adjuvants for symptom control in a range of conditions for which standard drugs are not fully satisfactory. Ashton *Addict. Biol.* 1999, 4(2): 111-26. Work has been limited, however, in relation to the design of CB2 ligands that do not confer psychotropic side effects. The slow pace of development in this regard has been due largely to a lack of information about the three-dimensional structures of the CB receptors and ligand binding sites.

Accordingly, need exists for CB2 chemical probes that can be used to distinguish the CB1 and CB2 pharmacophore features for structure-based design, and to identify novel CB2 selective ligands with the potential for development into therapeutic agents that have no psychotropic side effects.

SUMMARY OF THE INVENTION

In accordance with one aspect of the present invention, compounds are provided that possess the appropriate chemical scaffolds for selective CB2 biological selectivity. In one embodiment, a compound Formula I, a pharmaceutically acceptable salt of the compound of Formula I, a stereoisomer of the compound of Formula I, or a pharmaceutically acceptable salt of the stereoisomer of the compound of Formula I, are provided:

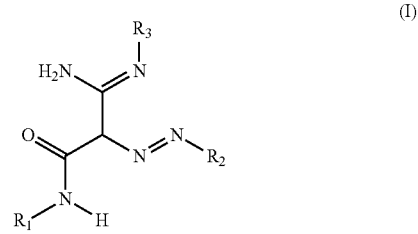

wherein;
R$_1$ is unsubstituted or substituted alkyl, unsubstituted or substituted aryl, unsubstituted or substituted cycloalkyl, unsubstituted or substituted cycloalkylalkyl, unsubstituted or substituted heterocyclyl, unsubstituted or substituted heterocyclylalkyl, unsubstituted or substituted aralkyl, unsubstituted or substituted heteroaryl, or unsubstituted or substituted heteroaralkyl;

R₂ is unsubstituted or substituted alkyl, unsubstituted or substituted aryl, or unsubstituted or substituted heteroaryl; and R₃ is unsubstituted or substituted alkyl, unsubstituted or substituted aryl, unsubstituted or substituted cycloalkyl, unsubstituted or substituted cycloalkylalkyl, unsubstituted or substituted heterocyclyl, unsubstituted or substituted heterocyclylalkyl, unsubstituted or substituted aralkyl, unsubstituted or substituted heteroaryl, or unsubstituted or substituted heteroaralkyl;

with the proviso that at least one of R₁ and R₃ is other than unsubstituted aralkyl, or R₂ is other than unsubstituted aryl.

In some embodiments of the compound of Formula I,

R₁ is a substituted or unsubstituted group selected from the group consisting of phenyl or naphthyl; cyclohexyl, cycloheptyl, cyclooctyl, bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl; pyrrolidinyl, imidazolidinyl, pyrazolidinyl, pyrrolyl, pyrrolinyl, imidazolyl, imidazolinyl, pyrazolyl, pyrazolinyl, piperidyl, piperazinyl, morpholinyl, thiomorpholinyl, pyranyl, quinuclidyl, indolyl, indolinyl, adeninyl, guaninyl, quinolinyl, isoquinolinyl, quinolizinyl, quinoxalinyl, or quinazolinyl; —(C1-C8 alkyl)phenyl; and pyridyl, pyridazinyl, pyrimidinyl, pyrazinyl, or benzothiophenyl;

R₂ is a substituted or unsubstituted group selected from the group consisting of C1-C8 alkyl; phenyl, naphthyl, and pyridyl; and/or R₃ is a substituted or unsubstituted group selected from the group consisting of C1-C8 alkyl, —(C1-C8 alkyl)phenyl, and —(C1-C8 alkyl)pyridyl.

In certain embodiments, R₁ of Formula I is substituted or unsubstituted group selected from the group consisting of phenyl, bicyclo[2.2.1]heptyl, benzyl, and morpholinyl; and/or R₂ is a substituted or unsubstituted group selected from the group consisting of propyl, butyl, and phenyl; and/or R₃ is a substituted or unsubstituted group selected from the group consisting of propyl, butyl, and benzyl. In other embodiments, the compound of Formula I has a group that is substituted is substituted with one or more of H, F, Cl, Br, SO₂, NO₂, OH, NH₂, or substituted or unsubstituted C₁-C₈ alkyl.

Pursuant to another aspect of the invention, the compound of Formula I is selected from the group consisting of:

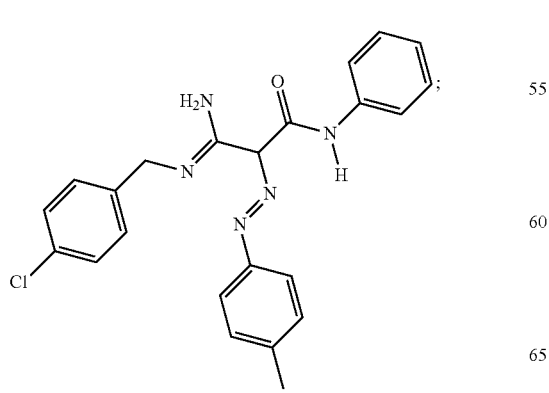

-continued

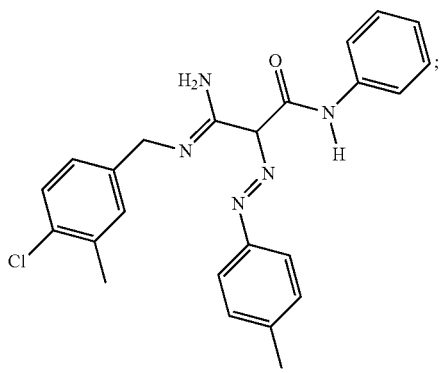

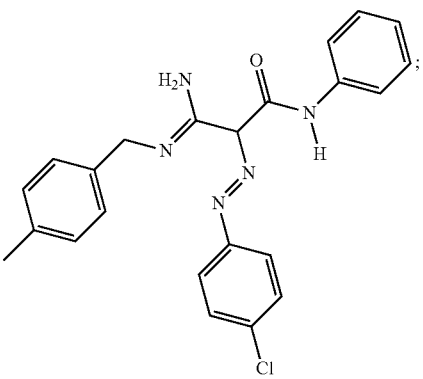

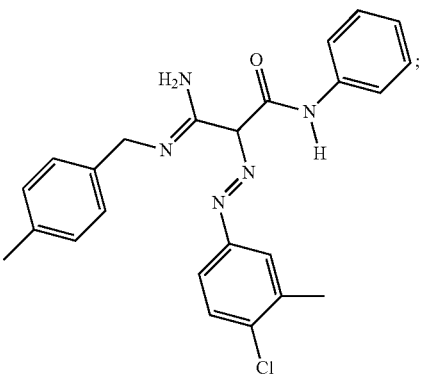

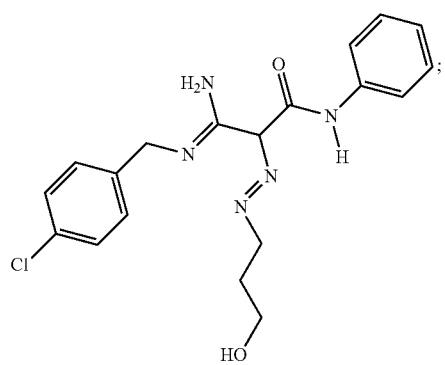
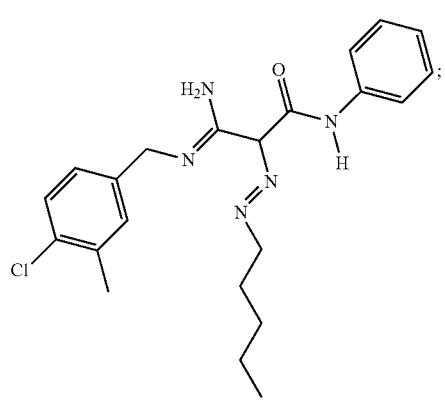
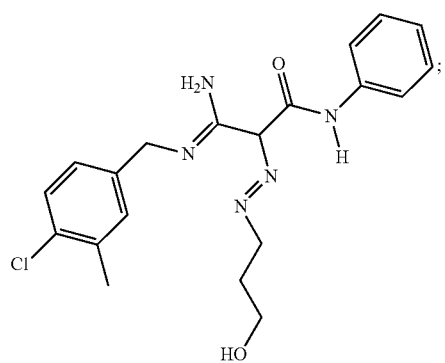
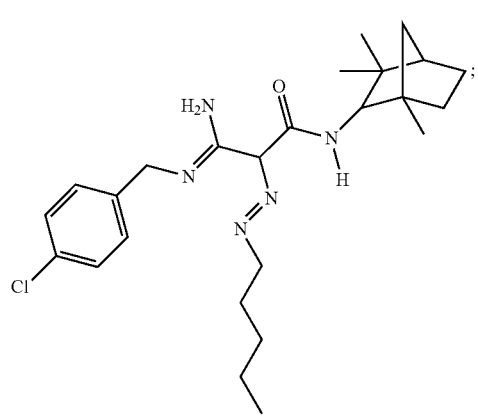
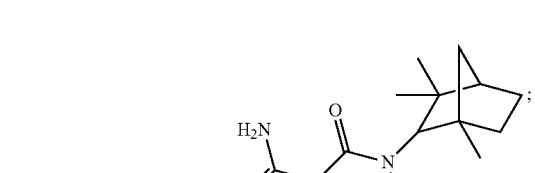
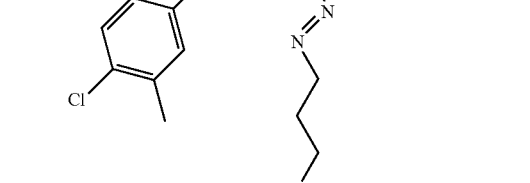
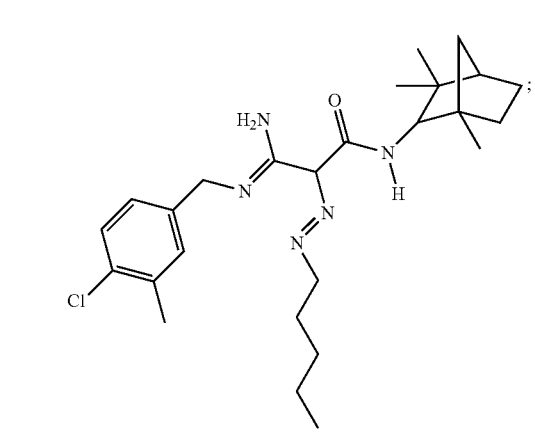
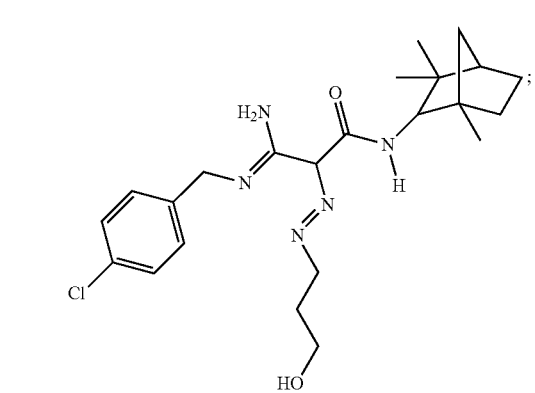
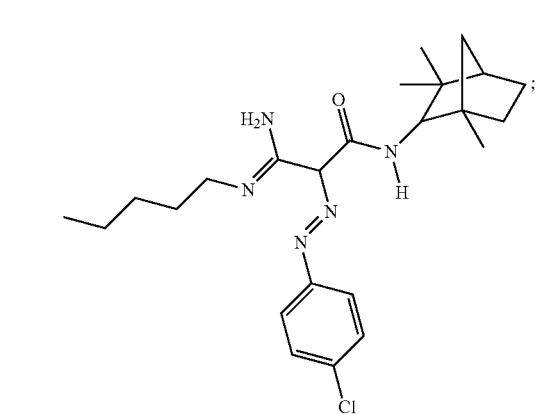

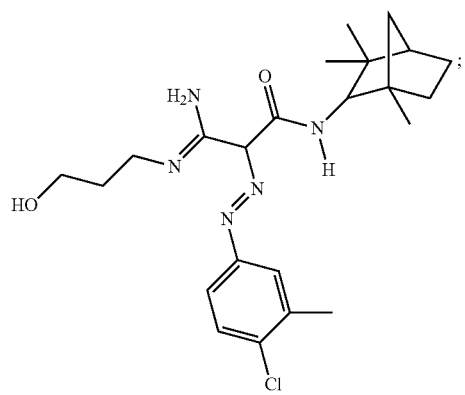
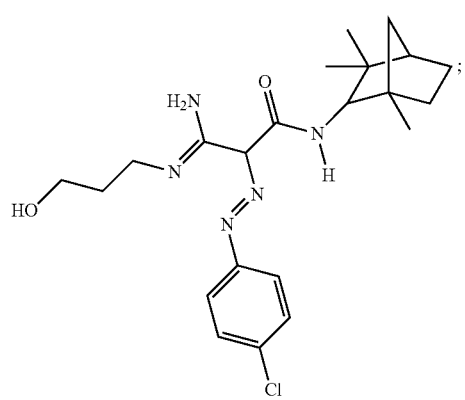
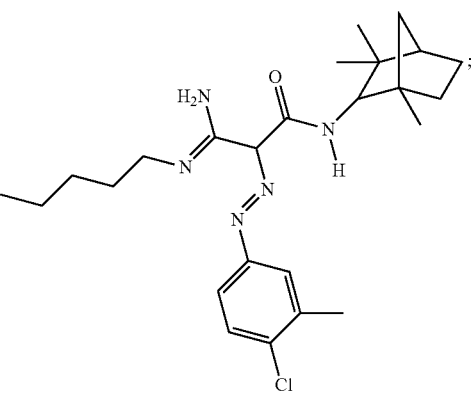
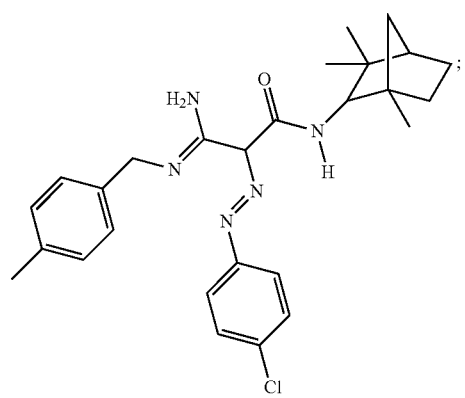
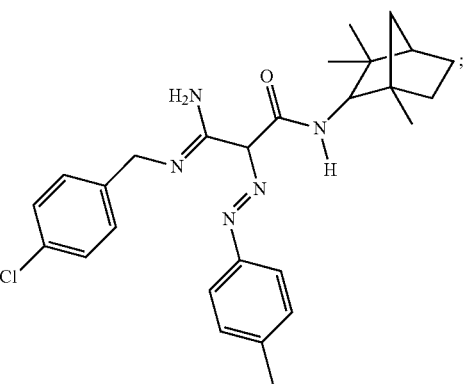
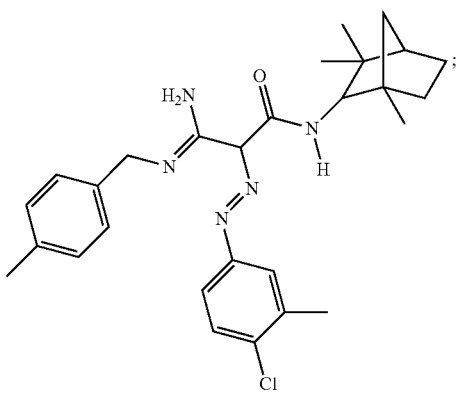
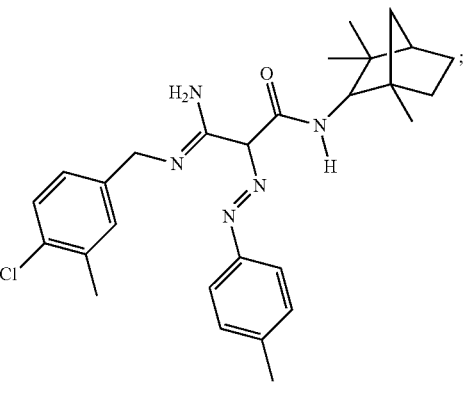
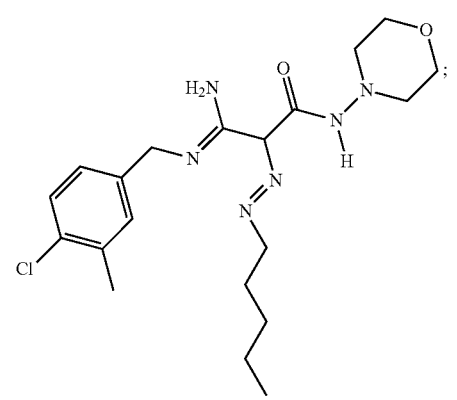

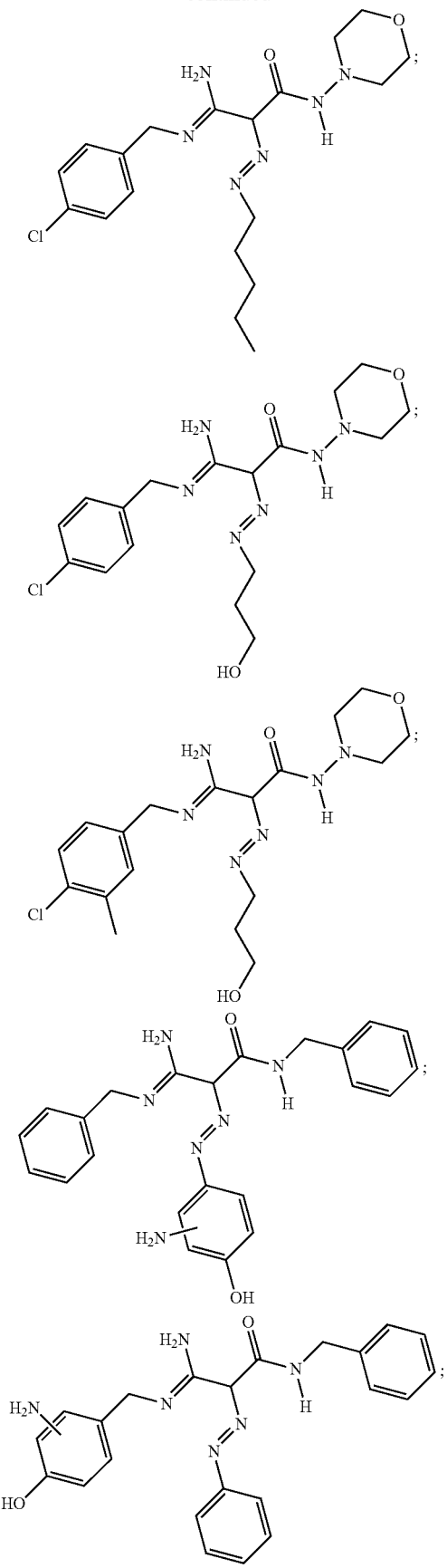

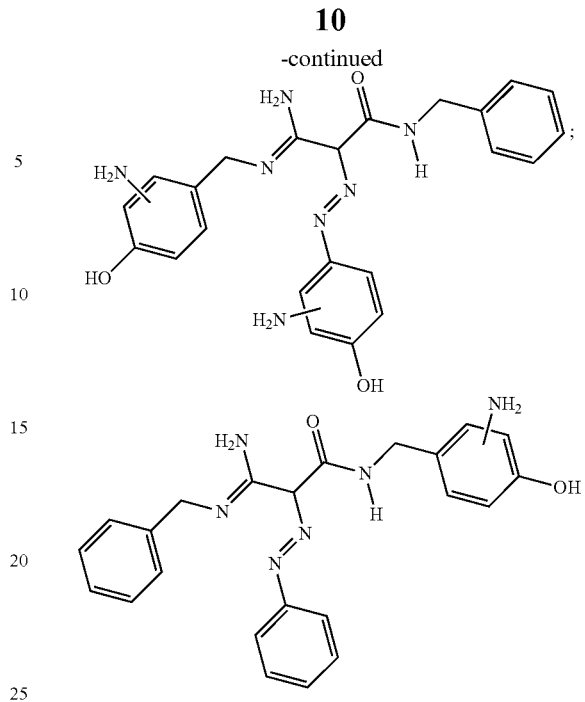

or a pharmaceutically acceptable salt thereof, a stereoisomer thereof, or a pharmaceutically acceptable salt of the stereoisomer thereof.

The present invention also comprehends a pharmaceutical formulations that comprises (A) a pharmaceutically acceptable carrier and (B) a compound of Formula I, a pharmaceutically acceptable salt of such compound, a stereoisomer of the compound, a pharmaceutically acceptable salt of such stereoisomer, a compound of Formula II, a pharmaceutically acceptable salt of the compound of Formula II, or a mixture of any two or more thereof. Formula II is shown below:

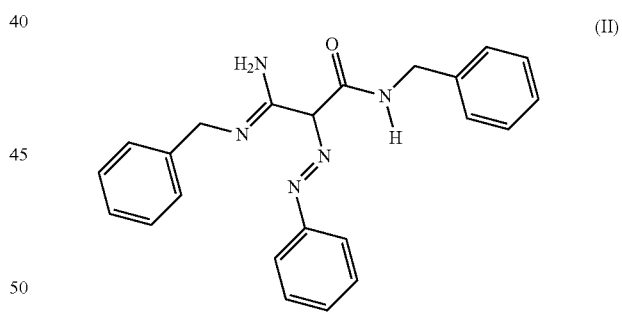

(II)

In another aspect, a method is provided that comprises inhibiting a cannabinoid receptor comprising administering a pharmaceutical formulation comprising a compound of Formula I, a pharmaceutically acceptable salt of the compound of Formula I, a stereoisomer of the compound of Formula I, a pharmaceutically acceptable salt of the stereoisomer of the compound of Formula I, Formula II, a pharmaceutically acceptable salt of the compound of Formula II, or a mixture of any two or more thereof, and a pharmaceutically acceptable carrier, to a subject. In some such embodiments, the cannabinoid receptor is cannabinoid receptor subtype-2. In other embodiments, the subject is in need of an anti-inflammatory agent.

In yet another aspect, methods are provided to determine the 3D structure and conformation of CB2 ligands. For example, in some embodiments, a method is provided comprising, using a compound of Formula I, a pharmaceutically acceptable salt of the compound of Formula I, a stereoisomer of the compound of Formula I, a pharmaceutically acceptable salt of the stereoisomer of the compound of Formula I, Formula II, a pharmaceutically acceptable salt of the compound of Formula II, or a mixture of any two or more thereof as an active fluorescence dye control for a fluorometric binding assay.

BRIEF DESCRIPTION OF THE DRAWINGS

FIG. 1A is CB2 binding $^3$H—CP 55940 (mouse spleen membrane) and FIG. 1B is CB1 binding $^3$H—CP 55940 (rat forebrain membrane).

DETAILED DESCRIPTION

Definitions

Figure 1:
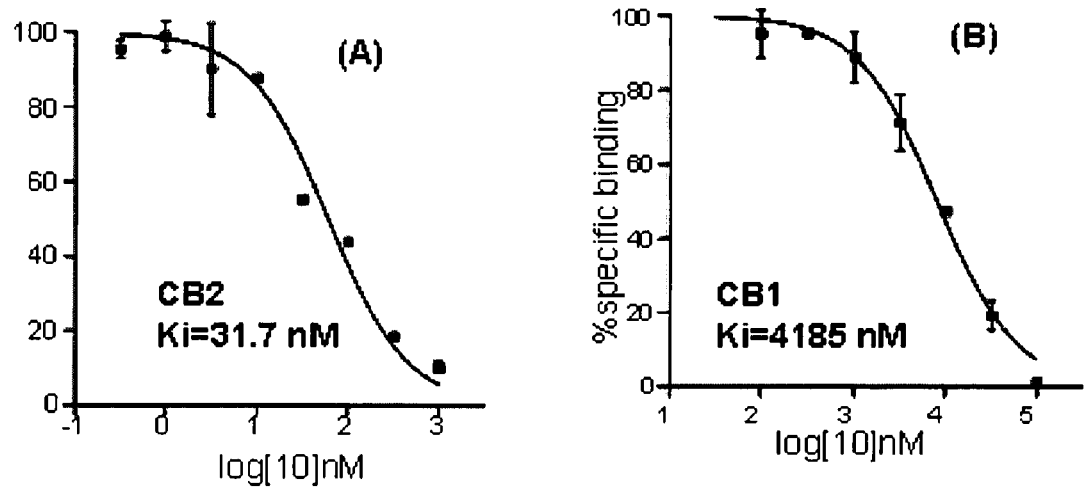
FIG. 1 presents two graphs of radiometric binding assay studies, showing that the compound of Formula II has high CB2 binding affinity, CB2 (31.7 nM) (A), but weak CB1 binding affinity, CB1 (4185 nM) (B).

For this disclosure and unless otherwise specified, "a" or "an" means "one or more."

As indicated above, "CB" is an abbreviation for "cannabinoid receptor." Similarly, "CB1" stands for "cannabinoid receptor subtype-1," and "CB2" for "cannabinoid receptor subtype-2."

Generally, reference to a certain element such as hydrogen or H is meant to include all isotopes of that element. For example, if an R group is defined to include hydrogen or H, it also includes deuterium and tritium. Accordingly, isotopically labeled compounds are within the scope of this invention.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. Representative substituted alkyl groups may be substituted one or more times with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkenylalkyl groups are alkyl groups as defined above in which a hydrogen or carbon bond of the alkyl group is replaced with a bond to a cycloalkenyl group as defined above. Substituted cycloalkylalkenyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-ethyl-indanyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups." Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl(pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, 4-ethyl-morpholinyl, 4-propylmorpholinyl, furan-2-yl methyl, furan-3-yl methyl, pyridine-3-yl methyl, tetrahydrofuran-2-yl ethyl, and indol-2-yl propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the invention are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the invention are not referred to using the "ene" designation. Thus, chloroethyl is not referred to here as "chloroethylene."

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "amine" (or "amino") as used herein refers to —NHR$^4$ and —NR$^5$R$^6$ groups, wherein R$^4$, R$^5$ and R$^6$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is NH$_2$, methylamino, dimethylamino, ethylamino, diethylamino, propylamino, isopropylamino, phenylamino, or benzylamino.

Those of skill in the art will appreciate that compounds of the invention may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

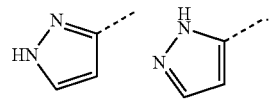

As readily understood by one skilled in the art, a wide variety of functional groups and other structures may exhibit tautomerism, and all tautomers of compounds as described herein are within the scope of the present invention.

Stereoisomers of compounds, also known as "optical isomers," include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

"A pharmaceutically acceptable carrier" is a phrase that denotes a carrier such as but not limited to a diluent, an excipient, a wetting agent, a buffering agent, a suspending agent, a lubricating agent, an adjuvant, a vehicle, a delivery system, an emulsifier, a disintegrant, an absorbent, a preservative, a surfactant, a colorant, a flavorant, a sweetener, or a mixture of any two or more thereof. Pharmaceutically acceptable excipients and carriers are generally known and, hence, are included in the instant invention. Such materials are described, for example, in REMINGTON: THE SCIENCE AND PRACTICE OF PHARMACY, 21$^{st}$ ed., The University of Philadelphia (2005).

The instant invention also provides for pharmaceutical compositions and medicaments which may be prepared by mixing one or more compounds of the invention, prodrugs thereof, pharmaceutically acceptable salts thereof, stereoisomers thereof, tautomers thereof, or solvates thereof, with pharmaceutically acceptable carriers, excipients, binders, diluents or the like to prevent and treat disorders associated with cannabinoid receptors. The compounds and compositions of the invention may be used to prepare formulations and medicaments that prevent or treat a variety of disorders associated with cannabinoid receptors, and described herein. For example, disorders and diseases such as obesity, smoking addiction, cardimetabolic risk factors, and other disorder and diseases associated with the central nervous system.

Illustrative of the forms suitable for such compositions are granules, powders, tablets, capsules, syrup, suppositories, injections, emulsions, elixirs, suspensions or solutions. A composition of the invention can be formulated for various routes of administration, for example, by oral, parenteral, topical, rectal, nasal, or vaginal administration, or via implanted reservoir. Parenteral or systemic administration includes but is not limited to subcutaneous, intravenous, intraperitoneally, intramuscular, intra-articular, intrasynovial, intrasternal, intrathecal, intralesional and intracranial injections. The following dosage forms are given by way of example and should not be construed as limiting the instant invention.

As noted, the invention comprehends pharmaceutically acceptable salts of the compounds described here. A compound of the invention has a number of basic nitrogen groups; hence, pharmaceutically acceptable salts can be formed with inorganic acids (such as hydrochloric acid, hydroboric acid, nitric acid, sulfuric acid, and phosphoric acid), organic acids (e.g., formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). The compounds of the present invention may have acidic substituent groups, and in such cases, it can form salts with metals, such as alkali and earth alkali metals (e.g., $Na^+$, $Li^+$, $K^+$, $Ca^{2+}$, $Mg^{2+}$, $Zn^{2+}$), organic amines (e.g., ammonia, trimethylamine, triethylamine, pyridine, picoline, ethanolamine, diethanolamine, triethanolamine) or basic amino acids (e.g. arginine, lysine and ornithine).

Certain compounds within the scope of the invention are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., *Methods in Enzymology* 112: 309-23 (1985); Bodor, N., *Drugs of the Future* 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), Goodman and Gilmans, THE PHARMACOLOGICAL BASIS OF THERAPEUTICS, 8th ed., McGraw-Hill (1992).

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Compounds

In one aspect, a compound of Formula I is provided, having the following structural formula:

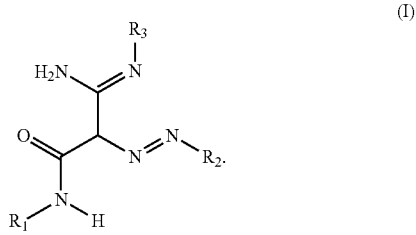

(I)

In the compound of Formula I, $R_1$ is unsubstituted or substituted alkyl, unsubstituted or substituted aryl, unsubstituted or substituted cycloalkyl, unsubstituted or substituted cycloalkylalkyl, unsubstituted or substituted heterocyclyl, unsubstituted or substituted heterocyclylalkyl, unsubstituted or substituted aralkyl, unsubstituted or substituted heteroaryl, or unsubstituted or substituted heteroaralkyl. In the compound of Formula I, $R_2$ is unsubstituted or substituted alkyl, unsubstituted or substituted aryl, or unsubstituted or substituted heteroaryl. In the compound of Formula I, $R_3$ is unsubstituted or substituted alkyl, unsubstituted or substituted aryl, unsubstituted or substituted cycloalkyl, unsubstituted or substituted cycloalkylalkyl, unsubstituted or substituted heterocyclyl, unsubstituted or substituted heterocyclylalkyl, unsubstituted or substituted aralkyl, unsubstituted or substituted heteroaryl, or unsubstituted or substituted heteroaralkyl. The compound of Formula I is also subject to the proviso, that at least one of $R_1$ and $R_3$ is other than unsubstituted aralkyl, or $R_2$ is other than unsubstituted aryl.

In some embodiments, $R_1$ is a substituted or unsubstituted group such as phenyl, naphthyl, cyclohexyl, cycloheptyl, cyclooctyl, bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, norbornyl, pyrrolidinyl, imidazolidinyl, pyrazolidinyl, pyrrolyl, pyrrolinyl, imidazolyl, imidazolinyl, pyrazolyl, pyrazolinyl, piperidyl, piperazinyl, morpholinyl, thiomorpholinyl, pyranyl, quinuclidyl, indolyl, indolinyl, adeninyl, guaninyl, quinolinyl, isoquinolinyl, quinolizinyl, quinoxalinyl, quinazolinyl, —(C1-C8 alkyl)phenyl, pyridyl, pyridazinyl, pyrimidinyl, pyrazinyl, or benzothiophenyl.

In other embodiments, $R_2$ is a substituted or unsubstituted group such as $C_1$-$C_8$ alkyl, phenyl, naphthyl, or pyridyl.

In yet other embodiments, $R_3$ is a substituted or unsubstituted group such as $C_1$-$C_8$ alkyl, —($C_1$-$C_8$ alkyl)phenyl, or —($C_1$-$C_8$ alkyl)pyridyl.

A non-limiting illustration of the compounds encompassed by Formula I, and the associated isomeric/tautomeric forms, includes:

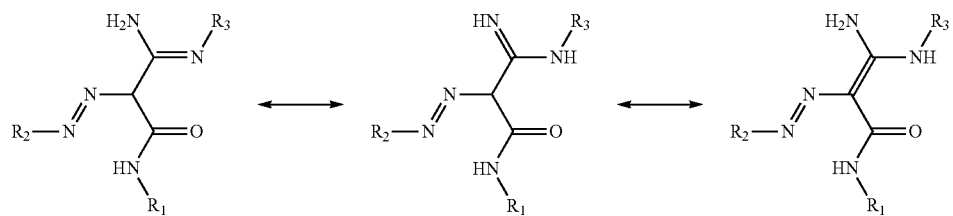

where the variable positions are defined in Table 1.

TABLE 1

| No. | $R_1$ | $R_2$ | $R_3$ | Note |
|---|---|---|---|---|
| 1 | phenyl | 4-Cl-phenyl | 4-CH₃-benzyl | Cl position is variable<br>CH₃ position is variable |
| 2 | phenyl | 4-CH₃-phenyl | 4-Cl-benzyl | Cl position is variable<br>CH₃ position is variable |
| 3 | phenyl | 4-Cl-phenyl | n-hexyl | Chain length is variable<br>Cl position is variable |
| 4 | phenyl | 4-Cl-phenyl | hydroxyalkyl | Chain length is variable<br>Cl position is variable |
| 5 | phenyl | phenyl | 4-OH-benzyl | OH position is variable |
| 6 | phenyl | 4-OH-phenyl | benzyl | OH position is variable |
| 7 | 4-OH-phenyl | phenyl | benzyl | OH position is variable |
| 8 | morpholinyl | 4-Cl-phenyl | n-hexyl | Chain length is variable<br>Cl position is variable |
| 9 | morpholinyl | 4-Cl-phenyl | hydroxyalkyl | Chain length is variable<br>Cl position is variable |
| 10 | bornyl | 4-Cl-phenyl | n-hexyl | Chain length is variable<br>Cl position is variable |
| 11 | bornyl | 4-Cl-phenyl | hydroxyalkyl | Chain length is variable<br>Cl position is variable |

TABLE 1-continued

| No. | R₁ | R₂ | R₃ | Note |
|-----|----|----|----|------|
| 12 | (norbornyl) | pentyl | -CH₂-C₆H₄-Cl | Chain length is variable; Cl position is variable |
| 13 | (norbornyl) | -(CH₂)₄-OH | -CH₂-C₆H₄-Cl | Chain length is variable; Cl position is variable |
| 14 | (norbornyl) | -C₆H₄-Cl | -CH₂-C₆H₄-CH₃ | Chain length is variable; Cl position is variable |
| 15 | (norbornyl) | -C₆H₄-CH₃ | -CH₂-C₆H₄-Cl | Chain length is variable; Cl position is variable |
| 16 | hexyl | -C₆H₅ | -CH₂-C₆H₅ | Chain length is variable; Cl position is variable |

In some embodiments, the compound of Formula I is represented by Formula III, or a pharmaceutically acceptable salt of the compound of Formula III:

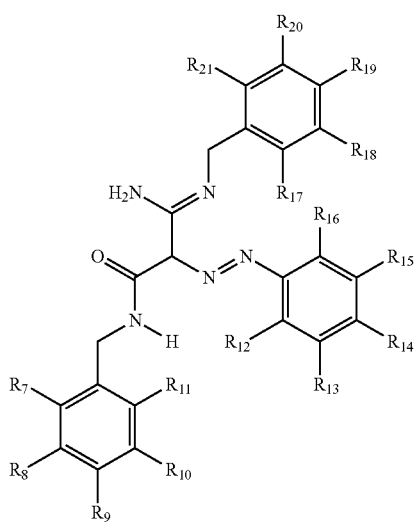

(III)

wherein $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ are individually H, F, Cl, Br, $SO_2$, $NO_2$, OH, $NH_2$, or substituted or unsubstituted $C_1$-$C_8$ alkyl. The compound of Formula III is also subject to the proviso of the compound of Formula I, such that at least one of $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ is other than H.

Compounds of the invention may be readily synthesized by techniques well known to those of skill in the art.

In another aspect, pharmaceutical compositions are provided. For example, pharmaceutical compositions of the compound of Formula I, a pharmaceutically acceptable salt of the compound of Formula I, a stereoisomer of the compound of Formula I, a pharmaceutically acceptable salt of the stereoisomer of the compound of Formula I, a compound of Formula II, a pharmaceutically acceptable salt of the compound of Formula II, or a mixture of any two or more thereof, and a pharmaceutically acceptable carrier are provided. The compound of Formula II has the following structure:

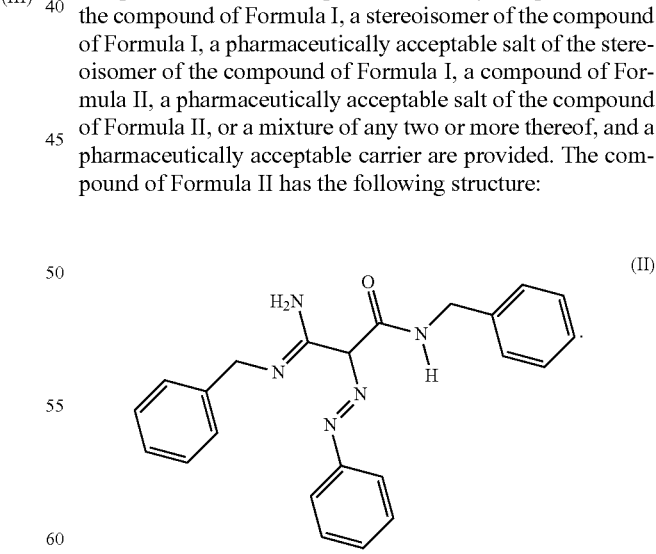

(II)

In yet another aspect, methods inhibiting a cannabinoid receptor are provided. Such methods may include administering the pharmaceutical compositions, provided herein, to a subject. Such subject may be in need of a cannabinoid receptor antagonist.

The compound of Formula II:

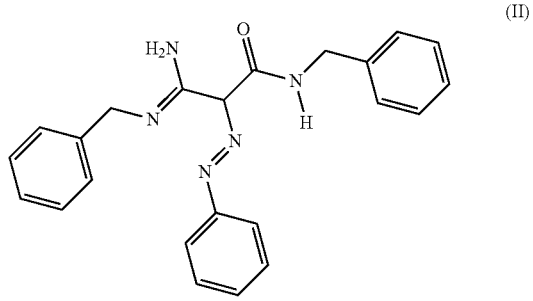 [SMILES: N/C(=N\Cc1ccccc1)C(/N=N/c1ccccc1)C(=O)NCc1ccccc1]

is a chemical probe with a high biological activity that selectively binds or interacts strongly with CB2. The compound of Formula II, has been shown to bind specifically to CB2. Such reactivity was shown using the knowledge-based cannabinoid (CB) ligand design approach, i.e., pharmacophore generation and in-silico database virtual screening as well as bio-validations. The compound of Formula II demonstrates nanomolar (nM) binding bioaffinity to the cannabinoid receptor subtype CB2.

In addition to binding CB, the compound of Formula II has been shown to be an active fluorescence dye with maximum fluorescence intensity at 485 nm. The fluorescence spectral measurements were done for the compound of formula II at 5.0 µM of a solution containing 25 mM Tris-HCl, 2.5 mM MgCl2, 1 mM EDTA. The sample was placed in a 3 ml fluorescence cuvette (excitation pathlength=10 mm) and spectrum recorded at 22° C. on a Cary Eclipse Fluorescence Spectrophotometer (Varian Inc.). The maximum fluorescence intensity was observed at 485 nm when the excitation wavelength was set at 468 nm and emission wavelength was started from 478 nm. The compounds of Formulas I and II fluoresce and may therefore be used as fluorescence image probes in binding assays for CB receptors. As such, the compounds of Formula I and/or Formula II may be reacted with a CB subtype 1 or 2 receptor, or a sample thought to contain a CB subtype 1 or 2 receptor. After, sample processing, the sample may then be assayed for the presence of the compound of Formula I and/or Formula II.

The compound of Formula II has strong CB2 specific binding activity and may also be used as an effective anti-inflammatory agent. It is known that CB2 receptor mediates signal transduction in the immune system, and CB2 ligands have the potential to be developed as drugs to treat a wide range of immune system disorders as well as chronic neuropains. See Correa F, Mestre L, et. al. The role of cannabinoid system on immune modulation: Therapeutic implications on CNS inflammation. *Mini-Reviews in Medicinal Chemistry* 2005, 5(7):671-675; Whiteside G T, et. al. The role of the cannabinoid CB2 receptor in pain transmission and therapeutic potential of small molecule CB2 receptor agonists. *Current Medicinal Chemistry* 2007, 14(8):917-936; and Howlett A C, et. al. Cannabinoid physiology and pharmacology: 30 years of progress. *Neuropharmacology* 2004, 47(Suppl. 1):345-358.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

In-silico Virtual Screening. Virtual screening studies were carried out on a Dell Cluster System consisting of 30 dual cores/dual nodes Xenon processors. 3D-QSAR studies of bioactive antagonists of the CB receptors were conducted, from which pharmacophore queries were developed by use of SPL scripts with DISCO and GALAHAD (Tripos programs) for 3D database search. See Chen et al. 3*D-QSAR Studies of Arylpyrazole Antagonists of Cannabinoid Receptor Subtypes CB*1 *and CB*2. *A Combined NMR and CoMFA Approach, Journal of Medicinal Chemistry* 2006, 49(2):625-636. The training database, consisting of 20 known active CB2 ligands and 980 random compounds, was established to examine and/or refine the generated pharmacophore hypotheses and to ensure the liability of the generated pharmacophore models. Subsequently, 3D pharmacophore database searches were carried out based on the pharmacophore queries generated above. The hit selections were done both manually and computationally in comparing with the actual pharmacophore models by the established scoring function and hit ranking algorithm. Such screening methods and other methods used herein are more fully described in Chen et al., *J. Chem. Inf. Model* 2007, 47: 1626-37. The compound of Formula II was one of the identified virtually CB2-active compounds, and was then further biologically validated using in-vitro radiometric binding assay below.

In-vitro Bio-validation Experiment. To biologically validate the screened hit compounds above, in-vitro [$^3$H]-radioactive CB ligand binding assays were carried out to determine the CB receptor binding affinity (Ki) of the screened ligands by displacing [$^3$H]-CP-55,940. The compound of Formula II was obtained from National Cancer Institute (NCI). For each assay, a positive control with a known ligand (SR-141716A for CB1 and SR-144528 for CB2) was run to ensure the reliability of the assay.

For CB1 receptor binding studies, rat forebrain membranes were prepared following the reported procedures. See Goutopoulos et al., *Bioorganic & Medicinal Chemistry* 2001, 9(7): 1673-84; and Mussinu, et. al., *Bioorganic & Medicinal Chemistry* 2003, 11(2):251-263.

For CB2 receptor binding studies, membranes were prepared from frozen mouse spleen. See Goutopoulos et al., *Bioorganic & Medicinal Chemistry* 2001, 9(7): 1673-84; Lin et al., *J Med Chem* 1998, 41(27): 5353-61; and Chin et al., *J. Pharmacol Exp Ther* 1999, 291(2):837-844.

The experiments were conducted based on reported procedures. See Lan et al., *AAPS PharmSci [online computer file]* 1999, 1(3):article 4; Abadji et al., *J. Med. Chem.* 1994, 37(120:1889-1893; and Abadji et al., *J. Neurochem.* 1999, 72(5):2032-38. Thus, the competition binding assay was performed using [3H]-CP-55,940 (1 nM) as a radioligand for the CB1 or CB2 cannabinoid receptor (rate brain or mouse spleen membranes), at 30° C. in 96-well microtiter plates, 50 μg of membrane each well re-suspended in 200 μl (final volume) binding buffer (50 mM Tris-HCl, 2.5 mM EGTA, 3 mM MgCl$_2$, 0.1% bovine serum albumin, pH 7.4). The tested compounds were presented at varying concentrations, and the nonspecific binding was determined in the presence of 10 μM CP-55,940 or HU-210. After 1 hr the incubation was terminated by rapid vacuum filtration through 96-well GF/B filter plates (PerkinElmer) on a PerkinElmer cell harvester and washed 5 times with one well-volume of ice-cold washing buffer (same as binding buffer except 0.5% bovine serum albumin). The filters were dried and the radioactivity on the filters was measured in a PerkinElmer TopCount Microplate Scintillation Counter using 30 μl of MicroScint-20 PerkinElmer. Assays were performed in duplicate or triplicate wells of the 96-well microtiter plates. The K$_i$ values were calculated by using GraphPad Prism 5.0 (GraphPad Software, Inc.).

Figure 2:
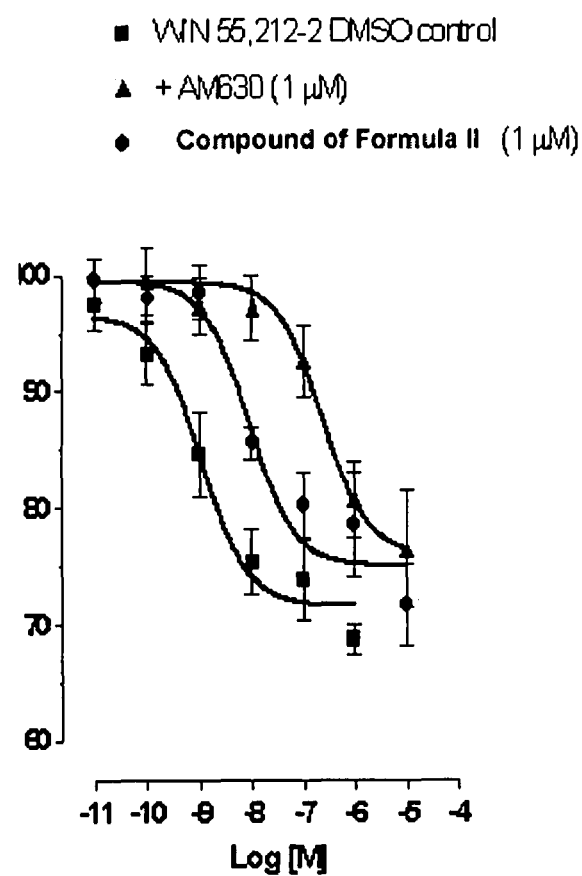
FIG. 2. Confluentially growing CB2 receptor transfected human CHO-K1 cells were stimulated with forskolin (20 μM) and analyzed for cAMP expression after 30 min. The CB2 agonist WIN55, 212-2 was incubated at increasing concentrations 30 min prior to forskolin stimulation alone or in presence of 1 μM of the antagonists AM630 and the compound of Formula II. The compound of Formula II, like AM630, inhibits the effect of WIN55,212-2.

Cell-based Functional Bioassay Studies. The nanomolar-binding affinity of the compound of Formula II have been illustrated using the $^3$H-radiometric binding assay shown in FIG. 1. Subsequently, further receptor biological studies were performed: i) to examine/assess the G-protein effects of the compound of Formula II upon CB2 receptor binding and ii) to test the compound of Formula II for anti-inflammatory effects. These studies confirmed that the compound of Formula II appears to be an antagonist like the known CB2 antagonist AM630 (but weaker), inhibiting the effect of the CB2 agonist WIN55212-2 in the forskolin-stimulated cAMP assay experiments as shown by FIG. 2.

Figure 3:
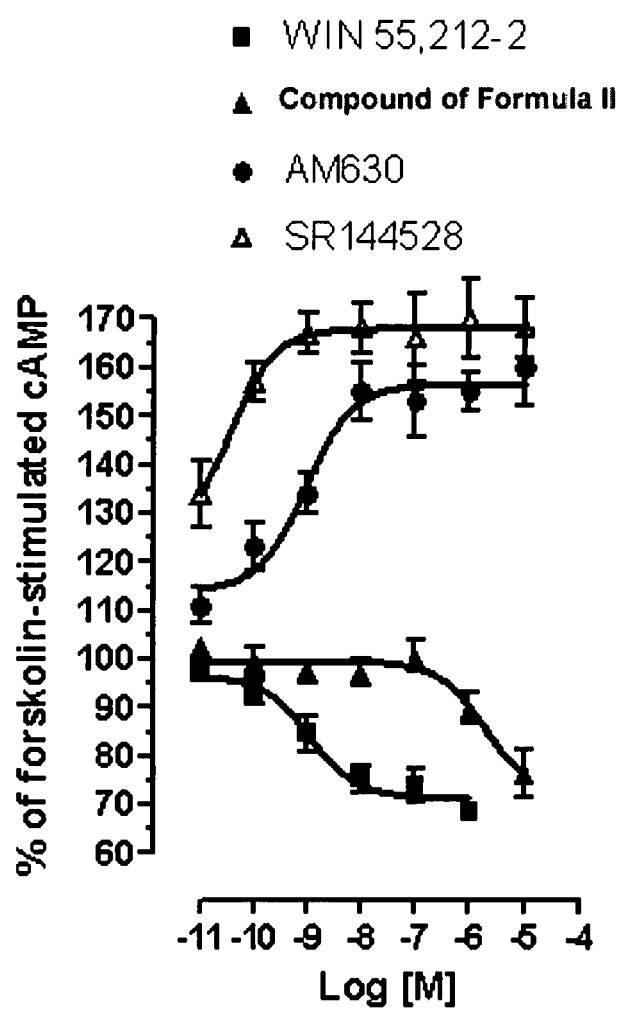
FIG. 3. Confluentially growing CB2 receptor transfected human CHO-K1 cells were stimulated with forskolin (20 μM) and analyzed for cAMP expression after 30 minutes. CB2 ligands were incubated at increasing concentrations 30 minutes prior to forskolin stimulation. AM630 and SR144528 are inverse agonist. The compound of Formula II is a weak agonist at high concentration (>7 mM) but also a antagonist when incubated with WIN55, 212-2, see FIG. 2.

Interestingly, however, the compound of Formula II is not an inverse agonist like the other known CB2 antagonists (e.g., AM630 and SR144528). The further cAMP measurement (FIG. 3) shows that the compound of Formula II behaves as a real antagonist by blocking cAMP effects but becomes an agonist at higher (~10 μM) concentrations.

The compound of Formula II acts as an antagonist by inhibiting cAMP but acts as a weak agonist at higher μM concentrations. Unlike the known CB2 inverse agonists, our compound does not have an impact on Gi-proteins at concentrations up to low μM and does not affect Go signaling. It should be pointed out that such concentration-dependent dual antagonist-agonist effects have also been reported for other receptors, e.g., neurotensin receptor, acetylcholine receptor, 5-HT1 receptor, and dopamine receptor. Cusack et al., *Molecular Pharmacology* 1993, 44(5):1036-1040; Schlicker et al., *Pharmacol Toxicol.* 1988, 63(4):281-285; and Mulder et al., *Eur. J. Pharmacol.* 1985, 107(3):291-297. According to R. Seifert's book "GPCR as Drug Targets," most GPCR antagonists on the market are inverse agonists but not true antagonists like our compound the compound of Formula II. Thus, the compound of Formula II is a unique CB2 chemical probe and offers a new avenue to explore the CB2 ligand binding biological mechanism. Seifert et al., in METHODS PRINC. MED. CHEM., vol. 24 (Wiley-VCH, 2005).

While several, non-limiting examples have been illustrated and described, it should be understood that changes and modifications can be made therein in accordance with ordinary skill in the art without departing from the invention in its broader aspects as defined in the following claims.

What is claimed is:

1. A compound of Formula I, a pharmaceutically acceptable of the compound of Formula I, a stereoisomer of the compound of Formula I, a pharmaceutically acceptable salt of the stereoisomer of the compound of Formula I:

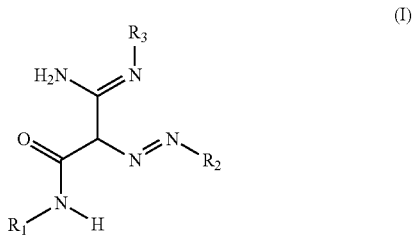

wherein;

R$_1$ is unsubstituted or substituted alkyl, unsubstituted or substituted aryl, unsubstituted or substituted cycloalkyl, unsubstituted or substituted cycloalkylalkyl, unsubstituted or substituted heterocyclyl, unsubstituted or substituted heterocyclylalkyl, unsubstituted or substituted aralkyl, unsubstituted or substituted heteroaryl, or unsubstituted or substituted heteroaralkyl;

R$_2$ is unsubstituted or substituted alkyl, unsubstituted or substituted aryl, or unsubstituted or substituted heteroaryl; and R$_3$ is unsubstituted or substituted alkyl, unsubstituted or substituted aryl, unsubstituted or substituted cycloalkyl, unsubstituted or substituted cycloalkylalkyl, unsubstituted or substituted heterocyclyl, unsubstituted or substituted heterocyclylalkyl, unsubstituted or substituted aralkyl, unsubstituted or substituted heteroaryl, or unsubstituted or substituted heteroaralkyl;

with the proviso that at least one of R$_1$ and R$_3$ is other than unsubstituted aralkyl, or R$_2$ is other than unsubstituted aryl.

2. The compound of claim 1, wherein;

R$_1$ is a substituted or unsubstituted group selected from the group consisting of phenyl, naphthyl cyclohexyl, cycloheptyl, cyclooctyl, bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl; pyrrolidinyl, imidazolidinyl, pyrazolidinyl, pyrrolyl, pyrrolinyl, imidazolyl, imidazolinyl, pyrazolyl, pyrazolinyl, piperidyl, piperazinyl, morpholinyl, thiomorpholinyl, pyranyl, quinuclidyl, indolyl, indolinyl, adeninyl, guaninyl, quinolinyl, isoquinolinyl, quinolizinyl, quinoxalinyl, quinazolinyl, —(C$_1$-C$_8$ alkyl)phenyl, pyridyl, pyridazinyl, pyrimidinyl, pyrazinyl, and benzothiophenyl;

R$_2$ is a substituted or unsubstituted group selected from the group consisting of C$_1$-C$_8$ alkyl, phenyl, naphthyl, and pyridyl; and R$_3$ is a substituted or unsubstituted group selected from the group consisting of C$_1$-C$_8$ alkyl, —(C$_1$-C$_8$ alkyl)phenyl, and —(C$_1$-C$_8$ alkyl)pyridyl.

3. The compound of claim 1, wherein R$_1$ is a substituted or unsubstituted group selected from the group consisting of phenyl, bicyclo[2.2.1]heptyl, benzyl, and morpholinyl.

4. The compound of claim 1, wherein R$_2$ is a substituted or unsubstituted group selected from the group consisting of propyl, butyl, and phenyl.

5. The compound of claim 1, wherein R$_3$ is a substituted or unsubstituted group selected from the group consisting of propyl, butyl, and benzyl.

6. The compound of claim 1, wherein the compound of Formula I is selected from the group consisting of:

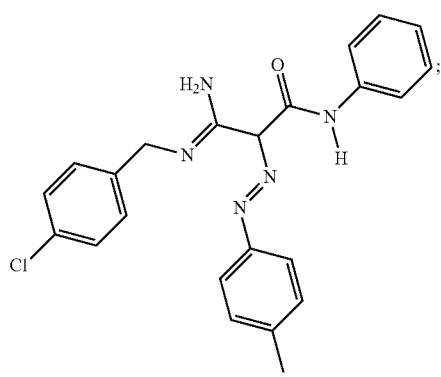
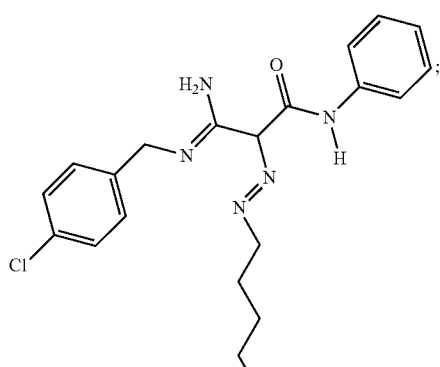
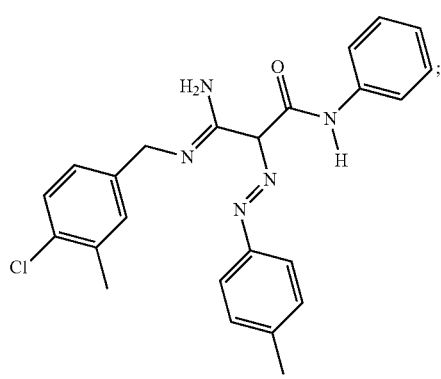
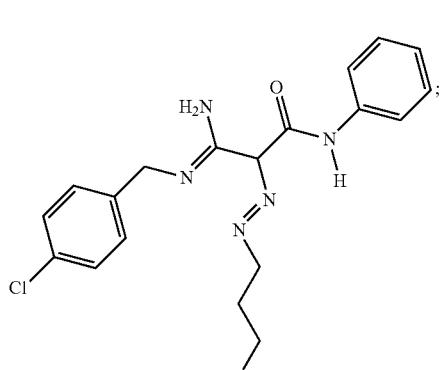
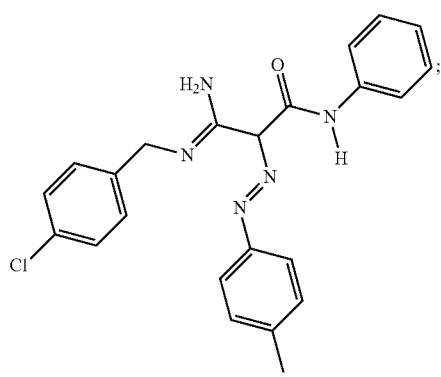
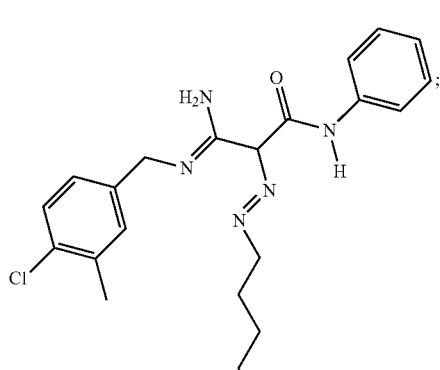
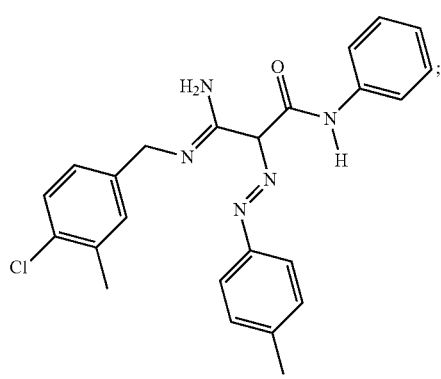
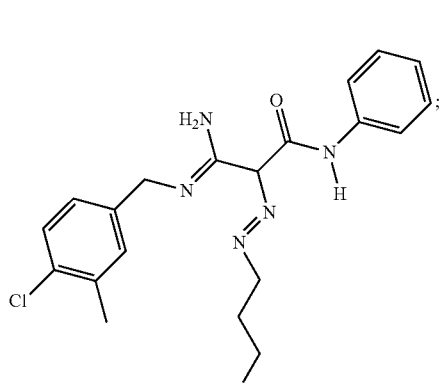

29
-continued
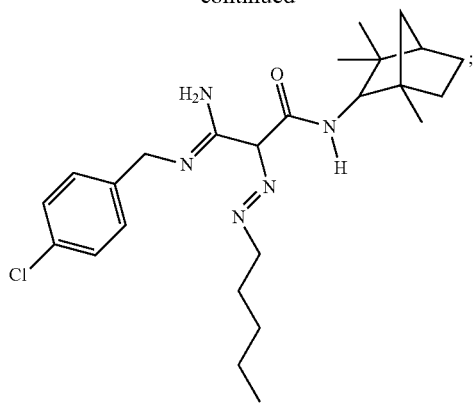
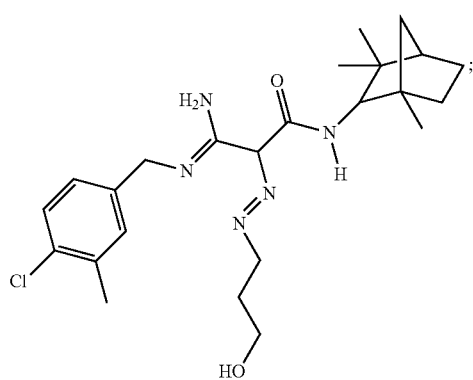
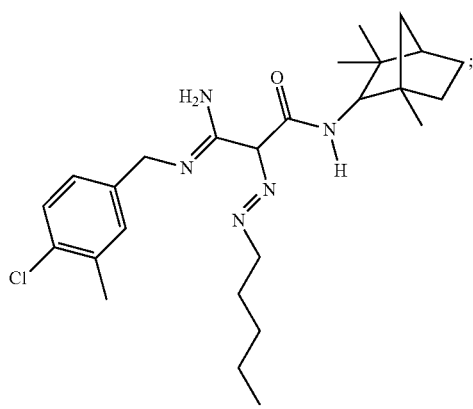
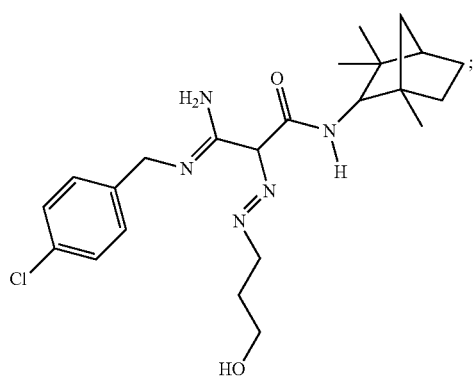
30
-continued
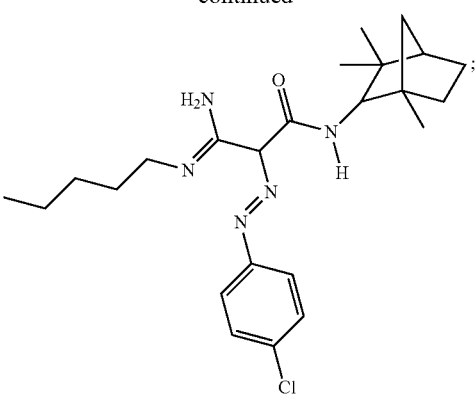
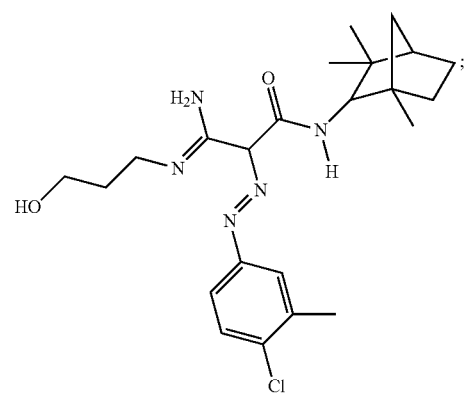
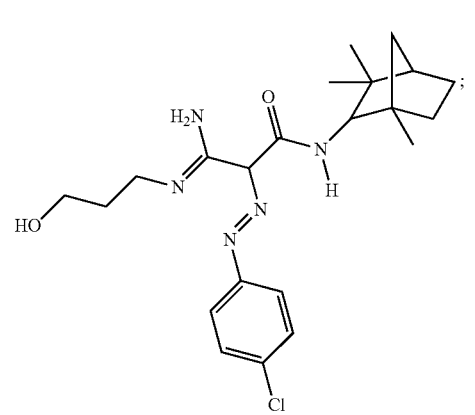
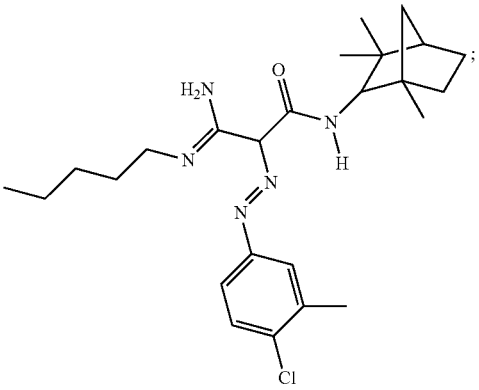

-continued
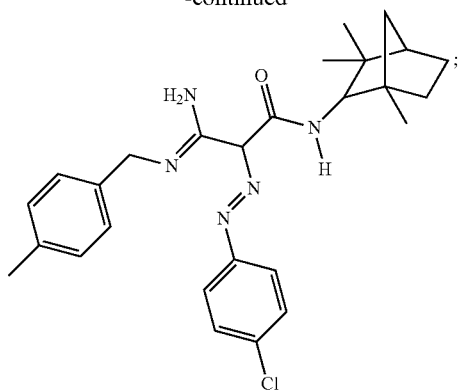
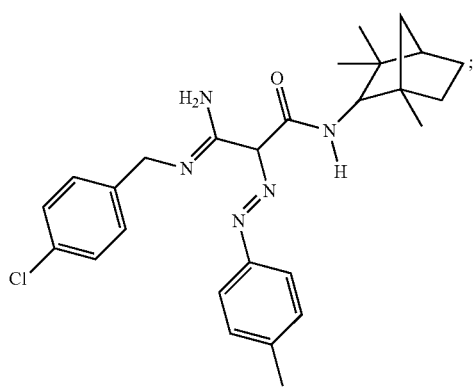
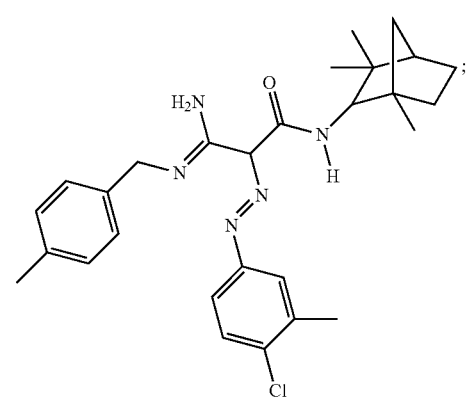
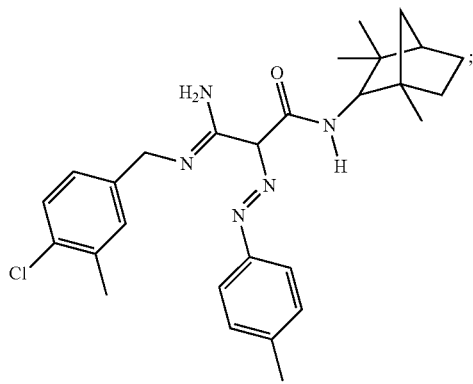
-continued
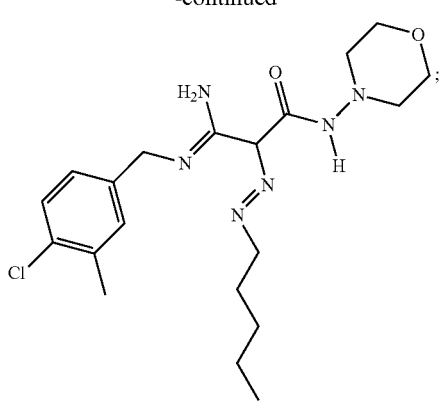
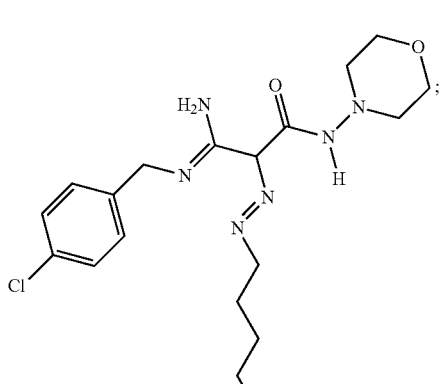
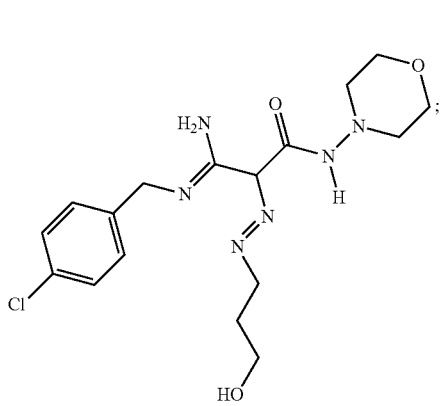
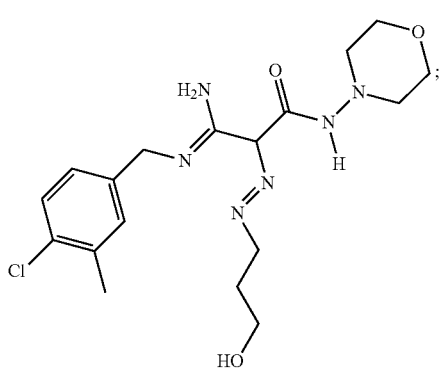

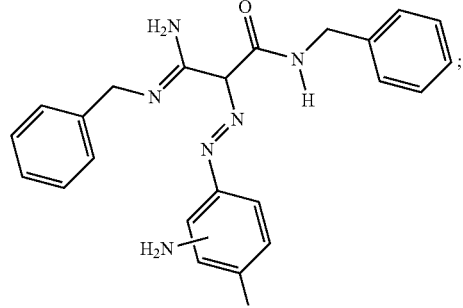

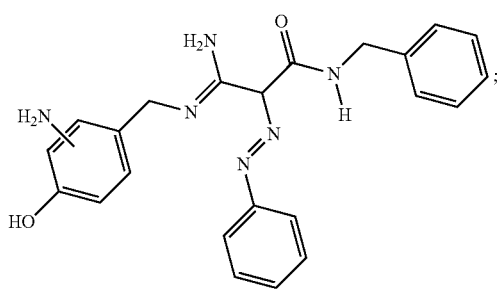

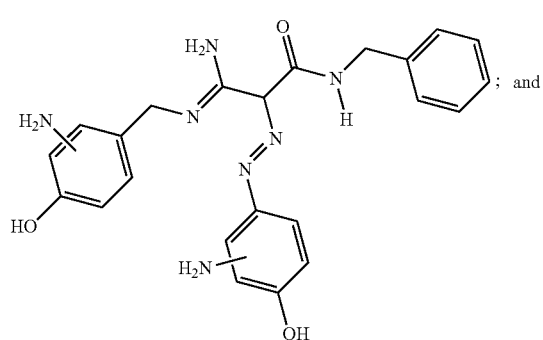

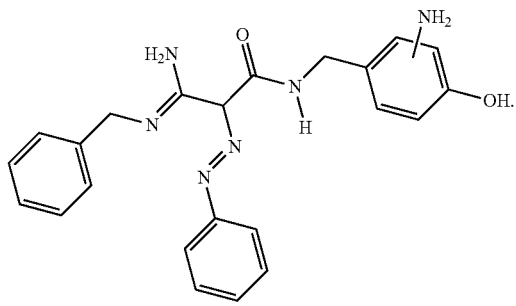

7. The compound of claim 1, wherein the compound of Formula I is represented by Formula III:

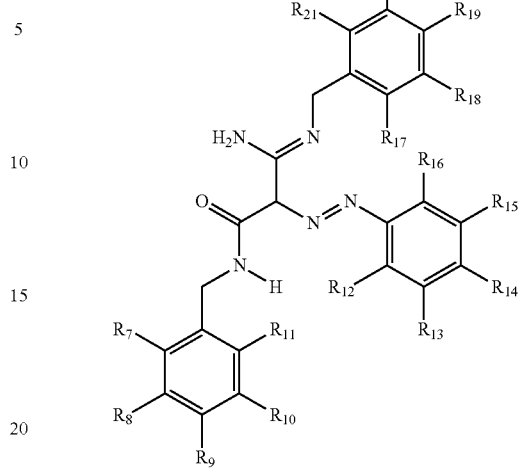

(III)

wherein
$R_7, R_8, R_9, R_{10}, R_{11}, R_{12}, R_{13}, R_{14}, R_{15}, R_{16}, R_{17}, R_{18}, R_{19}, R_{20}$, and $R_{21}$ are individually selected from the group consisting of H, F, Cl, Br, $SO_2$, $NO_2$, OH, $NH_2$, and substituted or unsubstituted $C_1$-$C_8$ alkyl,
with the proviso that at least one of $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ is other than H.

8. A pharmaceutical composition comprising the compound of claim 1, a stereoisomer thereof the compound of Formula I, a pharmaceutically acceptable salt of the stereoisomer of the compound of Formula I, a pharmaceutically acceptable salt of the compound of Formula I, a compound of Formula II, a pharmaceutically acceptable salt of the compound of Formula II, or a mixture of any two or more thereof, and a pharmaceutically acceptable carrier;

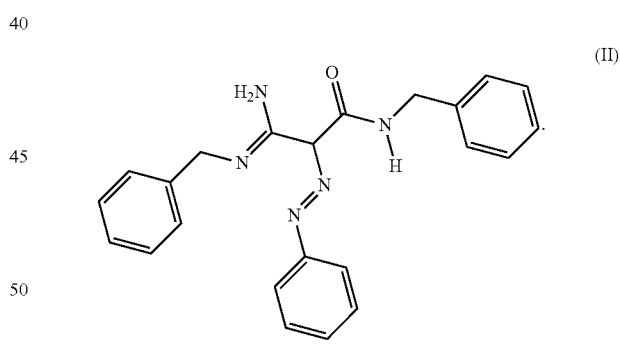

(II)

9. A method comprising inhibiting a cannabinoid receptor comprising administering the pharmaceutical composition of claim 8 to a subject.

10. The method of claim 9, wherein the cannabinoid receptor is cannabinoid receptor subtype-2.

11. A method comprising administering the pharmaceutical composition of claim 8 to a subject in need of an anti-inflammatory agent.

12. A method comprising using the compound of claim 1, a pharmaceutically acceptable salt of the compound of Formula I, a stereoisomer of the compound of Formula I, a compound of Formula II, or a mixture of any two or more thereof as an active fluorescence dye control for a fluorometric binding assay;

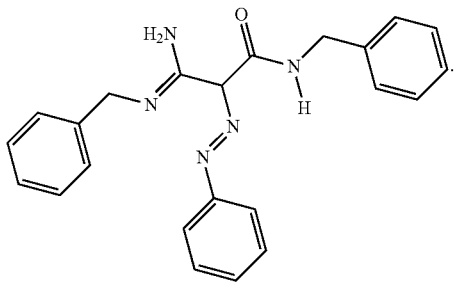

(II)

13. A pharmaceutical composition comprising the compound of Formula II, a pharmaceutically acceptable salt of the compound of Formula II, or a mixture thereof, and a pharmaceutically acceptable carrier;

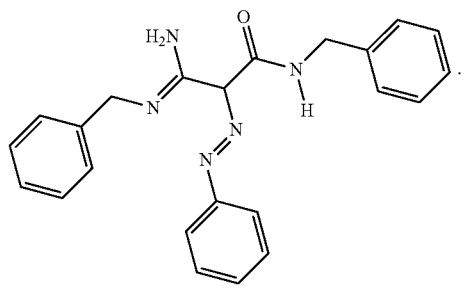

(II)

14. A method comprising inhibiting a cannabinoid receptor comprising administering the pharmaceutical composition of claim 13 to a subject.

15. The method of claim 14, wherein the cannabinoid receptor is cannabinoid receptor subtype-2.

16. A method comprising administering the pharmaceutical composition of claim 13 to a subject in need of an anti-inflammatory agent.

17. An active fluorescence dye control for a fluorometric binding assay, the active fluorescence dye control comprising a compound of Formula II, a pharmaceutically acceptable salt of the compound of Formula II, or a mixture thereof;

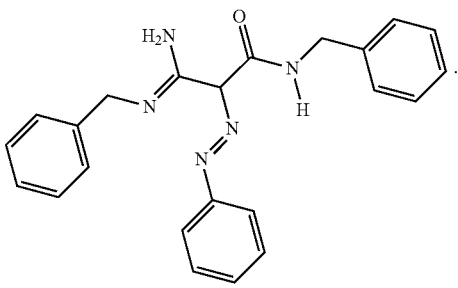

(II)

* * * * *

UNITED STATES PATENT AND TRADEMARK OFFICE
CERTIFICATE OF CORRECTION

PATENT NO.        : 8,466,131 B2         Page 1 of 1
APPLICATION NO.   : 12/740099
DATED             : June 18, 2013
INVENTOR(S)       : Xie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 416 days.

Signed and Sealed this
Eighth Day of September, 2015

Michelle K. Lee
*Director of the United States Patent and Trademark Office*